United States Patent
Alt

Patent Number: 5,143,089
Date of Patent: Sep. 1, 1992

[54] ASSEMBLY AND METHOD OF COMMUNICATING ELECTRICAL SIGNALS BETWEEN ELECTRICAL THERAPEUTIC SYSTEMS AND BODY TISSUE

[76] Inventor: Eckhard Alt, Eichendorffstrasse 52, 8012 Ottobrunn, Fed. Rep. of Germany

[21] Appl. No.: 517,186

[22] Filed: May 1, 1990

[30] Foreign Application Priority Data

May 3, 1989 [DE] Fed. Rep. of Germany ....... 3914662

[51] Int. Cl.$^5$ .............................................. A61N 1/05
[52] U.S. Cl. ..................................... 128/784; 128/642
[58] Field of Search ............... 128/639, 640, 641, 642, 128/784, 785, 786, 419 P, 419 D

[56] References Cited

U.S. PATENT DOCUMENTS

| | | | |
|---|---|---|---|
| 4,102,331 | 7/1978 | Grayzel et al. | 128/640 |
| 4,166,469 | 9/1979 | Littleford | 128/784 |
| 4,198,991 | 4/1980 | Harris | 128/784 |
| 4,506,673 | 3/1985 | Bonnell | 128/784 |
| 4,548,203 | 10/1985 | Tacker, Jr. et al. | 128/784 |
| 4,567,900 | 2/1986 | Moore | 128/784 |
| 4,574,814 | 3/1986 | Buffet | 128/786 |
| 4,998,975 | 3/1991 | Cohen et al. | 128/419 D |

FOREIGN PATENT DOCUMENTS

| | | | |
|---|---|---|---|
| 122258 | 2/1972 | Denmark | 128/641 |
| 3633803 | 4/1987 | Fed. Rep. of Germany . | |
| 2446001 | 9/1980 | France | 128/786 |
| 263239 | 12/1988 | German Democratic Rep. . | |
| 1219017 | 1/1971 | United Kingdom | 128/784 |
| 2157178 | 10/1985 | United Kingdom . | |

OTHER PUBLICATIONS

Stgrrenburg et al., "Carbon Fiber as an Electrode Material", IEEE Trans Biomed Eng. vol. BMB29, No. 5, May 1982, 352-355.

James et al., "Carbon Fibre Microelectrodes", J. Neuro. Methods, 1, No. 3, Oct. 1979, 279-287.

Newsweek, Jun. 18, 1979, p. 77-78.

Mund et al., "Development . . . Pacemakers", Siemens Forsch, pp. 227-234, 1979.

Watkins, Jr. et al., "Automatic defibrillation in men", Thoracic & Cord. Surg., 82:492-500, 1981.

*Primary Examiner*—Lee S. Cohen
*Attorney, Agent, or Firm*—Leitner, Greene & Christensen

[57] ABSTRACT

This invention provides improved electrode structures for electrically communicating between electrical therapeutic equipment and internal body tissue. Bundles of highly flexible, highly electrically conductive, preferably non-metallic carbon based, isotropically conductive fibers of diameters of the individual fibers in the micron range provide very large surface areas to apply electrical energy to the body tissue. Substantially non-electrically polarizing properties, particularly of carbon, and a substantially non-thrombogenic surface (present in carbon) represent critical features of the tissue to electrode interface in biomedical applications. Thus, more reliable-longer life implants of heart defibrillators, neurostimulators and the like result. This electrode structure with accompanying integrated electrical lead is implantable by puncture through body tissue thereby avoiding major surgery and general anesthesia required in the prior art. Accordingly the invention relates to the electrode and accompanying more effective therapeutic equipment as well as methods of therapeutic treatment with electrical current technology.

21 Claims, 2 Drawing Sheets

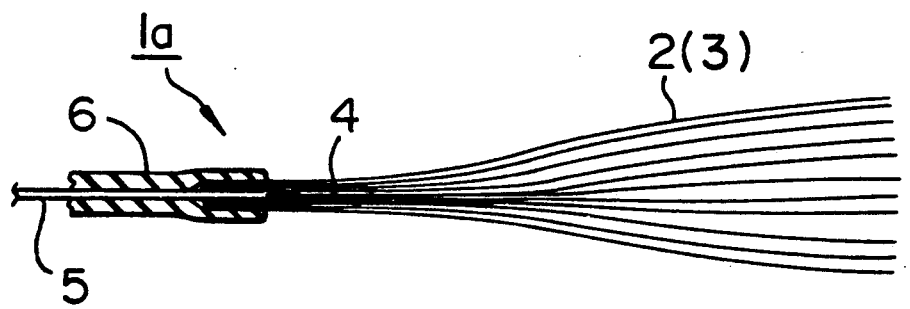
FIG. 1
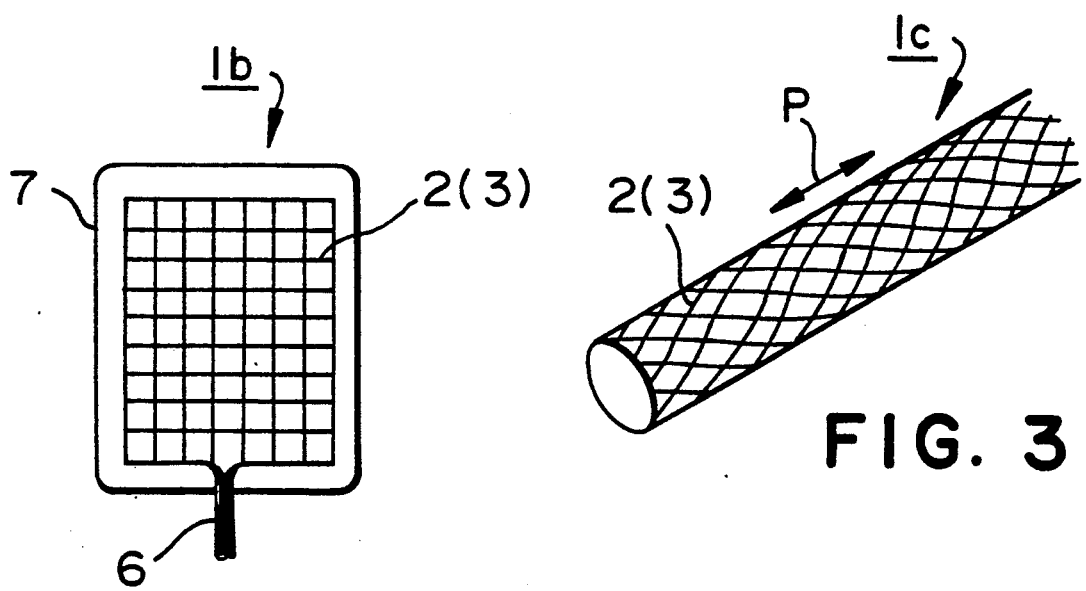
FIG. 2
FIG. 3
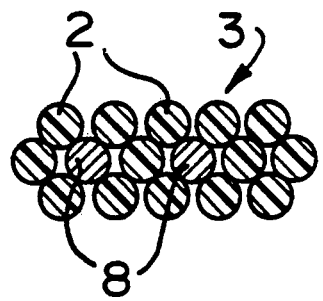
FIG. 4

ASSEMBLY AND METHOD OF COMMUNICATING ELECTRICAL SIGNALS BETWEEN ELECTRICAL THERAPEUTIC SYSTEMS AND BODY TISSUE

TECHNICAL FIELD

The present invention relates generally to means and methods for communicating electrical signals between electric therapeutic systems and devices and electrically excitable body tissue, and more particularly it relates to improved electrodes for interfacing with human body tissue and resulting improved electrical therapeutic systems and methods including implanted defibrillators for heart control and neurostimulation systems and methods of introducing the electrodes into the body for electrical contact interfacing with body tissue in a therapeutic target region.

BACKGROUND ART

Modern microelectronics has allowed for considerable progress to be made in medical technology in the last thirty years. Due to the increasing miniaturization of electronic components, it has been possible to develop a number of implantable medical devices in recent years for perceiving electrical signals of the human body and providing electrical signals, e.g. in the form of energy shocks or pulses, thereby exerting an influence on biological processes within the human body. Such devices include e.g. implantable cardiac defibrillators or implantable devices for stimulating nerves or muscles, including so-called neurostimulators, which are intended to relieve chronic pain by overstimulating a certain neuromere. Other such devices are stimulators for restoring a muscle tone if endogenic nerve pathways have failed, e.g. in the case of paraplegia. These implantable devices also include so-called defibrillators, which can reestablish a regular cardiac rhythm in the case of ventricular fibrillation by providing an electric shock to the cardiac tissue. These implantable defibrillators save lives in the case of certain asrhythmias.

Defibrillation has been known for more than thirty years. In the early years, it served in particular to help a fibrillating heart back to its regular beating rhythm during open heart surgery; cf. J. B. Rosenbaum in Surgery, May 1955, pp. 712 and 713.

In the early 1980's, a defibrillator was implanted for the first time. Experiences with this implanted device can be found in the survey by L. Watkins et al.: Automatic defibrillation in man, in J. Thorac, Cardiovasc. Surg. 82, 1981, pp. 492 to 500. The implantation method, which has not changed essentially up to now, consisted in applying two electrodes to the myocardium after opening the chest cavity. In addition to this method, one already introduced in early years was that of applying to the heart a usually large-surface electrode, a so-called patch, and placing an opposite electrode transvenously in the vena cava or in the atrium or right ventricle. The surgical method used for this purpose world-wide is also described in the article by L. Watkins et. al. After opening the thorax one exposes the pericardium and the heart, so that one can sew on the patch electrode required for defibrillation.

Since the patients in need of an implantable defibrillator generally have a very poor pumping function of the heart, one must not underestimate the complications of such a great surgical operation. Along with the risks of general anesthesia, problems occurred in past years in particular with respect to the placing of the electrodes and with respect to inadequate energy release or stimulus threshold conditions which even made it necessary to explant the entire defibrillator. There were also wound-healing impairments, pocket infections and large hematomas in the pericardium as a result of the operation. Post and perioperative fatalities were described, and repeatedly an additional further deterioration of the cardiac pumping function due to the sewn on patch electrode. A survey of such problems is found in the article by D. Echt et al., Clinical experience, complications and survival in 70 patients with the automatic implantable cardioverter/defibrillator, in Circulation, vol. 71, no. 2, 1985, pp. 289 to 296.

The patent literature describes, in addition to the above-mentioned patch or pad electrodes, a number of other electrode constructions and arrangements as well as methods of defibrillation.

U.S. Pat. No. 3,614,955 together with reissue patents nos. 27,652 and 27,757 describe an electrode which is introduced into the right ventricle of the heart and serves there not only to give shocks but also to monitor the cardiac activity. An electrode for defibrillation that is also introduced into the right ventricle and disposed on a catheter is known from U.S. Pat. No. 3,942,536. However, these two methods have not gained acceptance in practice due to insufficient functioning.

U.S. Pat. No. 3,857,398 discloses the combination of a defibrillator with a demand pacemaker. The defibrillator is triggered by cardiogenic electrical signals which are perceived with an electrode. The triggering of a defibrillator on the basis of perception of the electrical and mechanical activity of the heart is described in U.S. Pat. No. 4,291,699. U.S. Pat. No. 4,641,656 describes a pad electrode provided on the myocardium in conjunction with a large-surface opposite electrode in the right ventricle, for distributing the current conduction evenly over different muscle areas of the heart. According to U.S. Pat. No. 4,548,203, two pairs of spatially remote electrodes are disposed on the myocardium, whereby ventricular fibrillation and tachyrhythmia can be controlled by two pulses at different times. An endocardial electrode having an electrical connection between different conductor structures with low resistance is described in U.S. Pat. No. 4,481,953. A transvenous electrode arrangement is also known from U.S. Pat. No. 4,355,646, in which an endocardial electrode with two electrode points in the ventricle and two electrode points in the atrium is connected by a triaxial lead with low electrical resistance to an implantable cardioverter or defibrillator, for optimally measuring the changes in impedance of the ventricle and allowing for cardioversion to be performed via the same electrode. U.S. Pat. No. 4,355,642 discloses a disk-shaped electrode arrangement suitable both for perceiving the cardiogenic beat and for defibrillation. According to U.S. Pat. No. 3,738,370, a bipolar coaxial catheter is placed in the atrium, the electrode points thereof being used to perform the defibrillation. In U.S. Pat. No. 4,708,145, a pad electrode is placed on the myocardium while an opposite electrode is disposed within the heart. By sequential stimulation one can therefore eliminate ventricular fibrillation. In U.S. Pat. No. 4,787,389, electrode points are also provided outside on the myocardium as well as in the atrium and in the ventricle. There is a possibility here of performing antitachycardiac stimulation and defibrillation of the heart jointly, coded pulses being provided by the defibrillator to protect the antitachycardiac pacemaker from being damaged by the defibrillation pulse. U.S. Pat. No. 4,774,952 describes a multiple electrode arrangement for improved concentration of the current in the muscular areas of the heart during defibrillation. A similar electrode arrangement having a plurality of electrodes attached to the myocardium is also known from Soviet author's certificate no. 1,263,260. By evenly disposing a plurality of heteropolar electrodes about the heart, one reduces the harmful effects of the current on the myocardial cells. British patent application no. 2,182,566 shows an elastic disk electrode which is applied to the myocardium and, thanks to its elasticity, can better follow the movements of the heart. U.S. Pat. Nos. 4,270,549 and 4,291,707 describe a pad electrode which can be attached to the myocardium. A fine titanium wire structure serves as an electrode pole, whereby the mean current density can be increased by applying lateral insulators. These patents also mention a method by which the patch electrode can be applied without opening the upper chest cavity. This is done with a spatula-like instrument which is introduced into the chest cavity through a cut. However, the dimensions of the electrode presented here make it necessary for this introducing instrument to be of considerable size, having a width of four to six centimeters and a thickness of one to three centimeters. It is understood that this kind of opertion also needs general asesthesia and cannot be performed simply under local anesthesia.

Other patent art representative of the state of the defibrillation art and implantable cardiac electrodes therefor include U.S. Pat. 4,765,341, M. M. Mower, et al. and 4,512,351 P. J. Pohndorf, and European patent application 0,317,490 T. J. Fogarty published May 24, 1989 based upon a U.S. priority date of Nov. 13, 1987.

None of this art has resolved the problems encountered in interfacing electrodes with body tissue for low resistance conductivity, large surface area, low polarization and little intrinsic stiffness with interchange of electrical signals over long life with the capacity for good communication and high current levels. Additionally it still remains complicated to introduce and manipulate prior art electrodes and associated electrical therapeutic instruments.

In particular, the methods and apparatus described in the aforesaid literature and patents have not been able to solve essential aspects and problems of defibrillation of the heart. The basic problem relates to the energy transmission from an electrical device to the excitable human tissue via the electrode arrangement. Excitable tissue is understood to refer to those cells whose membrane field strength can be affected by the application of an electrical current in such a way as to result in a depolarization of the cell.

In the case of a nerve this results in a transmitted pulse, while in the case of a muscle cell a transmitted contraction results. The basic problems of energy transmission between an implantable device and the excitable tissue are accordingly found, as described at the outset, not only in defibrillators but also in neurostimulators, muscle stimulators, cochlear implants, and the like.

On the other hand for implantable cardiac pacemakers the problem of transmitting the energy from the pacemaker electrode to the heart has been intensely investigated in the past. A survey of these problems can be found in the article by A. Ripart and J. Muciga: Electrode heart interface: definition of the ideal electrode, in PACE, vol. 6, Mar. 1983, pp.410 to 421. The energy transmission was acceptably solved by materials with low polarization and an electrode head at the tip of the pacemaker electrode having an internal surface enlargement. The surface area required for the energy exchange between the myocardial tissue and the electrode is 10 square millimeters on the average. This surface suffices for transmitting the pacemaker pulses with voltages between 2.5 and 5 volts to the heart and stimulating the latter to beat. The cardiogenic action can also be perceived via this electrode surface. Materials for such electrodes are platinum iridium, pyrolyzed carbon and similar solids. However, the conditions described there for cardiac pacing are completely different from those requirments to be met by electrode systems for defibrillation of the heart, since with defibrillation a manyfold surface (10,000 mm$^2$) is mandatory in order to apply voltages of several hundred volts to the heart.

One electrode example is set forth in German Democratic Republic patent No. 263,239 Oct. 30, 1987 wherein a heart pacing lead comprises a bundle of anisotropic carbon fibers, which are effective for transmission of the pulse along the longitudinal axis toward the heart tissue. These electrodes could never support the large electrically active surface area needed in defibrillators because of the very small point contact surface area with heart tissue and would have a tendency to erode in time biologically in the electrode to body interface. Furthermore, this point contact characteristic cannot reliably support electrical signal communication for neurostimulation or muscle stimulation for instance because of a relatively undefined region of communication in body tissue disposed over larger surface areas. There must therefore be in essence a joining of each body nerve junction with a point contact, which makes potential use of such electrodes prohibitive.

Unsolved problems arise in the case of defibrillation of the heart. Here, voltages between 500 and 2000 volts are required, depending on the energy release of the implanted defibrillator, to rectify the heart, that is in a state of chaotic excitation, and restore a regular beating activity by providing shocks and defibrillation. In order to couple such energies into the heart, the defibrillation electrodes must have a surface between 50 and 100 square centimeters to avoid local burns. Transvenously applied electrodes also have a surface between 4 and 20 square centimeters to ensure an even energy flow through the heart. The large surface for the energy exchange, however, is only one of many requirements with respect to an optimal energy transmission between an implantable defibrillator and the heart. Other requirements are low energy consumption due to nonpolarizing materials, and an even larger surface that can expand further, if possible, thereby contacting many structures of the heart. The electrode providing the energy exchange with the heart should furthermore be very flexible and also allow for myocardial contact upon movement of the heart. Such high flexibility also prevents any further restriction of the myocardial function, which is usually already restricted in these patients, whether with respect to the systolic pumping function or with respect to the diastolic relaxation. High flexibility would furthermore restrict a mechanically induced foreign-body reaction. Such improvements with respect to the energy transmission would also allow for more economical utilization of the available energy, thereby making it possible to use smaller implantable devices with a longer life without increasing the battery capacity. The electrode should furthermore be easy to apply in order to minimize the risk of the operation. If possible, the risks of a thoracotomy should be avoided, to put an end to the wound-healing impairments, hemorrhages in the pericardium and other infections occurring in the past. It is desirable to be able to apply an electrode to patients who have already been operated on several times, even if these patients have developed corresponding adhesions due to a previous thoracotomy. An easier application would also result in lower hospital costs and could also be performed in hospitals which do not have their own heart surgery departments. It is also desirable to make the application readily repeatable if, for example, a change in the course of the disease due to new infarctions alters the demands to be made on the electrode arrangement, necessitating e.g. a higher energy exchange.

DISCLOSURE OF THE INVENTION

The invention is therefore based on the problem of improving methods of electrical therapeutic treatment and associated electrodes and apparatus. The unsolved prior art problem of providing adequate electrical communication interfacing with body tissue is now solved by means of an electrode presenting relatively very large electrical surface contact between the biological tissue and the electrode. The electrode arrangement is flexible so that it can follow the spontaneous movements of the biological tissue, in particular during defibrillation of the heart. The electrode has critical properties which include little or no capacitance effect in order to avoid polarization, particularly when it consists of pure carbon, which also has very low thrombogenic surface effect and no foreign body effect when implanted. In particular the electrode comprises a fiber bundle which can dispose at the body tissue interface a plurality of separate fiber conductors, which isotropically conduct electrical current thus resulting in very large increases in surface contact area with body tissue. Furthermore, the electrode is dimensionally small, easy to apply with a low risk during the application and is capable of being placed in patients who have already undergone operations. The electrode is inserted into the body by puncture rather than by surgery, even in contact with heart tissue inside and outside surfaces. This can be done under only local anesthesia which in the last consequence will allow ambulatory implants of defibrillators that currently still need a hospitalization stay of several weeks.

Accordingly, the bidirectional transmission of electrical signals between the implantable medical device and the tissue is effected by electrodes consisting of many fine, electrically conductive, nonmetallic fibers- in particular synthetic, and preferably carbon fibers- which lie directly against the tissue and form a very large surface altogether due to their large isotropically conductive surface areas even with very small diameters. The high flexibility of the fibers ensures direct contact with the tissue, even if the latter changes its shape or surface, as does the heart during beating and respiration. Since they show no, or only minimal, polarization phenomena, the fibers allow for an economical utilization of available energies. Their biological inertia also prevents foreign-body reactions, which otherwise also impede the bidirectional signal transmission by fibrosis. Such fibers allow for an optimal perception of the electrical signals of the cell and for a low-loss energy transmission of the implantable medical device to the tissue to be excited. One can therefore implant therapeutic devices and systems for communicating with body tissue by means of the improved electrode. Such system implants may now be of small dimensions, even with smaller batteries now available which also have a longer life.

In recent years, electrically conductive polymers have been increasingly developed; of. H. Naarmann: Elektrisch leitfahige Polymere: Anwendungsspektrum noch nicht ausgereizt; special print from Chemische Industrie, No. 6/87, and H. Naarmann: Die elektrochemische Polymerisation, in Angewandte Makromolekulare Chemie 162, 1988, pp. 1 to 17, and U.S. Pat. No. 4,468,291, which describes a method for producing electrically conductive polypyrrole films.

In these electrically conductive carbon derivates, the addition of electron donors or acceptors and the reduction or oxidation of the matrix achieve a transition from insulator properties to conductor properties with a clear increase in the electron mobility and high electrical conductivity. These electrically conductive polymers have not only very good conductivities up to values of 100,000 siemens per centimeter, but also the property of being producible in very fine fibers. It is thus possible to produce polymer fibers with a thickness as low as 8 to 20 microns. Due to the small diameter of the individual fiber, a bundle of fibers has a very large surface. For example, a fiber bundle whose individual fibers are 12 microns thick and whose diameter is 2 millimeters has a total surface of 10 square centimeters per centimeter of bundle length. Such a fiber bundle with a length of only one centimeter can therefore replace a patch electrode with a surface of 10 square centimeters as used up to now for defibrillation. For use in connection with a defibrillator, one will of course not apply only one centimeter of such a fiber bundle to the myocardium, but use e.g. one or more fiber electrodes in the pericardial cavity having a length between 10 and 15 centimeters. This results in a total surface of 100 to 150 square centimeters on the theoretical assumption that all individual fibers are exposed. This can of course not be obtained in reality. However, since a certain amount of moisture always collects in the pericardium, the internal surface is clearly increased above the measure determined strictly geometrically by direct connection to the myocardium.

Such electrically conductive polymers are very flexible and have virtually perfect inertia due to their chemical carbon composition. Their exterior surfaces are smooth and are non-thrombogenic in nature so that human tissue does not tend to develop foreign-body reactions to them. Corresponding experiences with other forms of carbon implants from other medical areas, e.g. bone surgery, have confirmed this in the past.

Such fibers can also be formed into different configurations. It is possible to weave the fibers together, make fiber netting, weave the individual fibers into small chains or small bundles, or work them into small tubes. The weaving can impart elasticity for hugging body organs, such as the heart, for example. The flexibility of the electrodes produced therewith is very high. Thus they may be flexed in place with heartbeats, or may be moved about for placement or for feeding in greater lengths of conductive fibers. This is true for lead bundles, dispersed groups of individual fibers and two or three dimensional configurations of woven fibers, or the like.

The electrical properties of electrodes made of fibers or bundles of fibers have been specifically determined by the applicant in a number of tests. In a glass cylinder filled with a saline solution, various energies were transmitted between conventional electrodes used for defibrillation, e.g. a patch electrode with a length of six centimeters and a width of four centimeters, and an opposite electrode and compared with measurements in which the energies were transmitted between a novel electrode structure of this invention and an opposite electrode. The electrodes used were simple fiber bundles or tubular or flat electrodes woven from individual fibers. The energy yield was recorded with the aid of a computer system. Not only the time slope of the voltage curve was recorded, but also the time slope of the current curve, and from the integral was calculated the particular energy released by an external defibrillator to such a water bath system. It was shown that for the electrode configuration of this invention consisting of a fine bundle of synthetic fibers with a thickness of altogether two millimeters and a length of ten centimeters allows for an energy yield that is 20 to 30% higher, compared to a conventional patch electrode with outer dimensions of four by six centimeters. Also the maximum achievable voltage for a given energy level was found to be favorable over conventional patch systems. This is made possible, on the one hand, by the virtual lack of polarization in the material and, on the other hand, by the large surface of the small fiber structures. Patch electrodes made from a fiber fabric according to the invention also showed an energy yield improved by about 20% compared to conventional flat patch electrodes of the same size. The critical rise time of impulses was better because of low polarization (low capacity).

The energy transmission was investigated not only in numerous in vitro tests, but also in practical animal experiments. For example, defibrillation of an arrythmic and fibrillating pig's heart was successfully performed with half the energy required with a conventional prior art electrode arrangement. The electrode used was a fiber electrode inserted into the space between the pericardium and the myocardium.

Electrodes made of the electrically conductive, nonmetallic, carbonized polymer fibers of this invention can be used not only for energy transmission, however, but also for perceiving electrical signals of biological tissue. When tissue cells are depolarized, they release small currents with voltages in the range of millivolts. An electrode arrangement on or in the heart or in contact with other body tissue such as muscles or nerve centers, is then in a position to perceive these signals and pass them on via a lead to an implantable medical device. High conductivity in the electrode to body tissue interface is critical. After appropriate amplification and filtering, these signals can be used to control a therapeutic device or system externally located or implanted.

Thus the electrodes afforded by this invention are suitable for energy transmission from a defibrillator to the heart and for other therapeutic treatment systems and methods. These electrodes are used to excite muscle tissue, for example. Such methods are becoming increasingly important for paraplegic patients, in whom the normal innervation of the muscles still having a basically normal function is disturbed due to a transverse lesion and an absence of neural information. Implantable medical devices can conduct the coded muscle stimulation information to the muscle in such a way that the latter assumes different extended and bending positions within the total muscular apparatus. Previous experiences with externally applied electrodes have shown that such patients can even make first attempts to walk. However, the inventive fine fiber electrodes also allow for energy transmission in the implanted state, whereby these fibers can be brought to the desired place of stimulation within the muscle with the help of a guide catheter applied by puncture. The excitation of fine nerves is also possible with fine fiber electrodes according to the invention. The electrodes can be brought e.g. by microscopic operation methods to the corresponding nerves or brought in close contact with these nerves, also with nerves of the spinal marrow or the vagal nerve for control of epileptic seizures.

The implantation of an inventive electrode in connection with a defibrillator can be obtained by puncturing the pericardium, thereby avoiding a thoracotomy and a pericardiotomy. For this purpose the pericardial cavity is punctured by a fine needle through which a fine guide wire is introduced into the space between the pericardium and the beating heart. The needle primarily used for the puncture can thereafter be removed. Via the guide wire one can then introduce into the pericardial cavity an introducing catheter with a dilator. When the dilator is withdrawn and the guide wire removed, there is a lumen within the introducing catheter through which one can insert, for example, an electrode in the form of a fiber bundle according to the invention, which is in turn provided with a lead for a defibrillator implanted in the abdominal cavity. When the catheter is withdrawn and removed, only the defibrillation electrode is located between the pericardium and the myocardium. Since the fiber bundle fans open, a large contact area is created between the electrode and the heart.

Via the guide catheter one can also introduce other electrodes, e.g. woven tube electrodes or woven flat electrodes, whereby the latter are rolled together to such small dimensions, due to the fine fibrous material, that they can be introduced via the introducing catheter.

There is furthermore the possibility of placing a second guide wire in the introducing catheter after the latter has been inserted, so that a plurality of introducing wires and guide catheters can be applied through the same puncture site. The additional introducing catheters can be used to bring to the heart a plurality of such fiber bundles for defibrillation. The electrical leads for the individual electrodes can then be connected with the aid of a subcutaneous line to the defibrillator implanted in the abdominal cavity.

The described method for placing electrodes has the additional advantage that it can also be used in patients who have already undergone several heart and thorax operations. A new operation with a thoracotomy would involve a clearly increased risk that does not exist at all with the described puncture method.

This puncture method can also be used to apply electrodes to nerves or muscles for stimulation, or the like.

The puncture of the pericardium can be monitored e.g. with ECG control. As soon as the puncture needle, which is electrically connected to an ECG amplifier, reaches the heart or scratches it, there is a potential deflection on the measuring device of the ECG amplifier. The puncture needle is then slightly withdrawn accordingly, whereafter the catheter and the electrode are introduced. It is also possible to use echocardigraphic control, whereby a sterile ultrasound transmitter is placed on the chest, and the heart and the puncture needle represented on a monitor.

In some patients the pericardium adheres to the heart due, for example, to earlier inflammatory phenomena or previous operations. In this case the electrode, e.g. an electrode woven from fibers, can be stuck directly to the pericardium outside the pericardial sac. The control of the application takes place e.g. by mediastinoscopy.

A number of materials exist for making electrodes from fibers according to the invention. Examples are iodine-doped polyacythylene fibers, which have a conductivity of over 100,000 siemens per centimeter, sometimes with a high degree of crystallinity. Another starting material for conductive synthetic materials is the polymer polypyrrole. It is also favorable to use carbon or C fibers from the Celion company with diameters of 20 microns, which are connected to form thin fiber strands and may optionally then be woven together.

BRIEF DESCRIPTION OF THE DRAWING

The invention is explained in more detail in exemplary embodiments with reference to the drawing, in which FIG. 1 shows a schematic view of a fiber electrode according to the invention consisting of isotropically conductive fibers;

FIG. 2 shows a view of a two dimensional patch or pad electrode woven from fibers;

FIG. 3 shows a schematic view of a three dimensional tubular electrode woven from fibers;

FIG. 4 shows a cross-section of a fiber bundle combined of a plurality of fibers having therein markers opaque to radiant energy to facilitate X-rays or flouroscopy;

THE PREFERRED EMBODIMENTS

Figure 5:
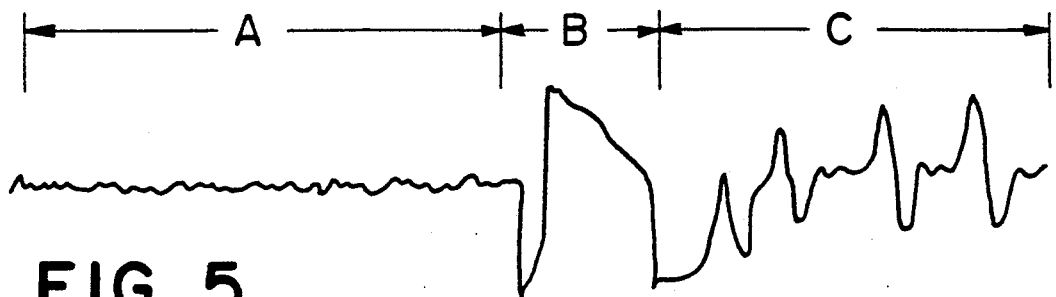
FIG. 5 shows a signal diagram during fiber effected defibrillation of a heart after ventricular fibrillation.

FIG. 1 shows, not true to scale, a fiber electrode 1a consisting of a plurality of electrically conductive polymer fibers 2 or fiber strands 3 as shown in cross section in FIG. 4. The fibers are combined at one end of the bundle to form a short rod 4 and connected there to an electrical conduction lead 5 within insulation 6, which for example may be connected with an implanted medical device or therapeutic instrument 19 (FIG. 6), e.g. a defibrillator, neurostimulator or muscle stimulator. Additionally or alternatively the fiber electrode may have a target body tissue area other than the heart 11 such as in an arm muscle or nerve center 11' where fiber electrode 1a' communicates by way of cable 6' with the therapeutic system 19 for receiving and sending electrical impulses.

Adjacent to rod 4, (FIG. 1) fibers 2 or fiber strands 3 are no longer interconnected, so that they can fan open, as schematically shown, thereby enlarging the contact surface on a tissue, e.g. the myocardium because of the isotropic conductivity of the fibers.

FIG. 2 shows a flat two dimensional electrode 1b which is woven with bundles of fibers 6 having a plurality of individual fibers 2 or fiber strands 3 according to FIG. 4. Insulated lead 6 is provided on one side of this electrode. The netting can be applied to a flexible electrically insulating carrier rim 7. This flexible carrier 7 provides e.g. on one surface electrical insulation of electrode 1b inserted between the pericardium and the heart with respect to the pericardium.

FIG. 3 shows a three dimensional tubular electrode 1c which is woven of individual fibers 2 or fiber strands 3. This tubular electrode can be compressed or drawn apart in accordance with double arrow P. As such it can surround and grasp a body organ, and is particularly useful in revised three dimensional configuration for encompassing a significant area on the outer surface of the heart in substantially elastic form as a defibrillation electrode. When the tubular electrode 1c is elongated, the diameter is reduced, which favorably permits passing the electrode through the hollow of a puncture needle, as described below in connection with FIG. 6. In the forms 1a and 1c for example, the fibers or fiber net may be flexed in-situ for better positioning or conductive contact with the target body tissue. The same tubular fiber configuration can be optionally applied also into the blood of the inner cavity of the heart and there serve as a counter-electrode also having a large surface area to encompass a short large area conductive path through heart tissue for defibrillation. This is possible since the electrode material is non thrombogenic.

FIG. 5 shows the electrical heart signal during defibrillation of a pig's heart, using a fiber electrode according to FIG. 1. The opposite electrode was a quadripolar endocardial electrode having two electrode points disposed in the atrium and two others in the ventricle of the heart. The electrical intracardiac heart signal was picked up from the body tissue contact by the fiber electrode. In time period A virtually no regular heart signal was detected, which signifies fibrillation by the baseline noise-like fibrillatory signal. An electric shock was then applied to the myocardium via the fiber electrode in time period B, whereupon the normal heart signal recurred in time period C.

Figure 6:
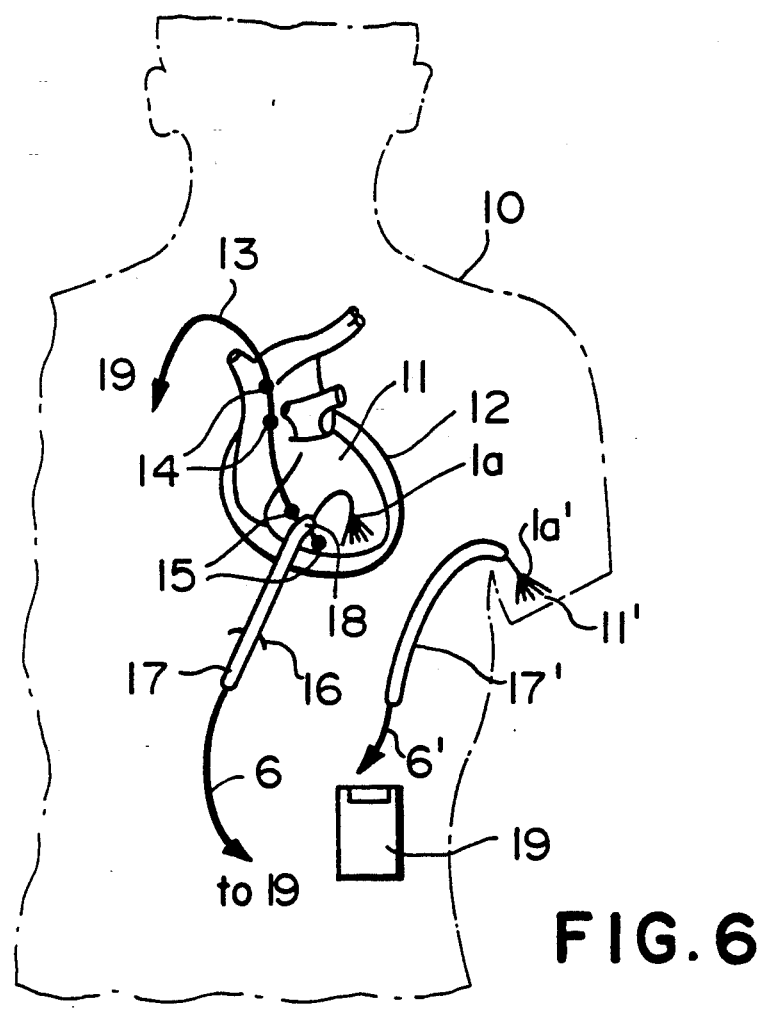
FIG. 6 shows a schematic view of an implanted system illustrative of the puncture method for applying a fiber electrode to body tissue according to the invention, in this example between the pericardium and the myocardium.

FIG. 6 shows part of the silhouette of a patient 10 with the position of heart 11 and pericardium 12 surrounding the heart. A probe 13 is introduced into the heart intravenously and bears two electrodes 14 in the atrium and another pair of electrodes 15 in the ventricle. These electrodes serve as opposite electrodes during defibrillation.

In accordance with this invention, the fiber bundle is inserted into a target tissue communication region by puncture, thereby avoiding general anesthesia and major surgery. Thus at a puncture site 16 a puncture needle is first introduced into the space between heart 11 and pericardium 12. A guide wire is then pushed into the puncture needle, whereafter the puncture needle is withdrawn. A guide catheter 17 is then pushed onto the guide wire, said catheter being slightly bent in the anterior area at 18 to allow for better placement of fiber electrode 1a to be introduced subsequently. The guide catheter has an interior dilator for expanding the passage through puncture site 16 and through the pericardium. After the dilator is removed, fiber electrode 1a with lead 6 is inserted through the guide catheter and placed accordingly. After the guide catheter is removed, which is e.g. a so-called peel-away catheter, lead 6 is guided subcutaneously up to a defibrillator 19 implanted in the abdominal cavity and connected there. Probe 13 is also drawn subcutaneously up to defibrillator 19.

By similar procedure, the electrode 1a' may be inserted into an alternative body tissue target site, such as the arm muscle as suggested at 11', or alternatively a nerve communication region such as the vagal nerve or spinal cord fiber branches.

In order to allow for exact detection of the position of fiber electrode 1a in subsequent X-ray examinations or in fluroscopy used for positioning, etc., fibers 2 of the fiber electrode are disposed e.g. about one or more flexible fibers 8 impenetrable to X-rays or otherwise opaque to radiant energy, as shown schematically in FIG. 4. The fibers or fiber strands alternatively may be doped or coated with materials impenetrable to X-rays.

I claim:

1. A method of therapeutic treatment of a living body, comprising the steps of:
   implanting into the body a flexible electrode consisting of multiple woven strands of tiny individual elongate uninsulated fibers composed of non-metallic substantially isotropic electrically conductive material electrically connected to a current-carrying lead, to form an electron-ion interface with blood and/or body tissue for efficient transfer of electrical energy along an entire substantial length of uninsulated surface of the fibers, in which the cumulative fiber surface presents an effective surface area considerably greater than the apparent actual surface area calculated from the linear dimensions of the electrode, and
   transmitting electrical impulses through the lead to the electrode at one side of said electron-ion interface to deliver electrical energy from the impulses to the other side of the interface with rapid initial rise times as a consequence of the electrical characteristics of the interface.

2. The method of claim 1, wherein
   the therapeutic treatment is defibrillation of the heart,
   the implanting step includes positioning the electrode adjacent to the epicardium of the heart,
   detecting ventricular fibrillation of the heart, and
   the transmitting step includes applying a defibrillating impulse to the lead in response to the detection of ventricular fibrillation of the heart to deliver a high energy shock to the heart with optimum efficiency across said electron-ion interface.

3. The method of claim 2, wherein
   the electrode is deployable in substantially two-dimensional shape, and
   the implanting step includes:
      puncturing the skin of the body, and
      introducing the electrode and the lead through the puncture for positioning the electrode in the desired location within the body, and
      deploying the electrode for optimum exposure of the surface area thereof in tissue excitable relation to a portion of the epicardium which is preselected to enhance the likelihood of defibrillation.

4. The method of claim 3, wherein
   the fibers of the electrode are interspersed with fibers composed of material opaque to radiation of the type employed for viewing the progress of a medical procedure within the body from a point external to the body, and
   the steps of introducing and deploying are performed while utilizing said viewing to observe the progress of positioning the electrode.

5. The method of claim 3, wherein
   the steps of introducing and deploying are performed to position the electrode inside the pericardium sac.

6. The method of claim 2, further comprising
   the step of intravenously introducing a second electrode, deployable in substantially three-dimensional shape of generally tubular configuration connected to a second current-carrying lead and otherwise having substantially the same composition and electrical properties as the first-mentioned electrode, into the heart to act as a counter electrode to the first-mentioned electrode during defibrillation.

7. The method of claim 6, wherein
   the detecting of ventricular fibrillation of the heart is performed using one of the first-mentioned electrode and the second electrode.

8. The method of claim 6, further comprising:
   shaping the second electrode, prior to the introducing step, by selectively interweaving the fiber strands thereof into said tubular configuration to allow the second electrode to flex by expansion and compression along the axis of the tubular configuration, whereby to permit the second electrode to expand axially to a reduced diameter for ease of introduction into the heart, and to relieve stresses on the second electrode when positioned within the heart which would otherwise subject it to fatigue and potential fracture.

9. The method of claim 1, further comprising:
   prior to the implanting step, shaping the configuration of the electrode by selectively interweaving the fiber strands thereof according to the general shape of the body tissue with which the electrode is to interact electrically at the desired location within the body.

10. The method of claim 9, wherein
    the shaping step comprises the step of interweaving the fiber strands into a two-dimensional configuration.

11. The method of claim 9, wherein
    the shaping step comprises the step of interweaving the fiber strands into a three-dimensional configuration.

12. The method of claim 1, wherein
    substantially all of the fibers comprise a carbon derivative possessing the property of substantially isotropic electrical conductivity, rendering the surface of the electrode substantially non-thrombogenic and said electron-ion interface of relatively low polarization, low capacitance, low resistance and low impedance.

13. An implantable lead assembly for biomedical use in a living body to stimulate and/or sense electrical excitation of selected excitable tissue in the body when the lead assembly is implanted, comprising:
    an electrically conductive lead,
    electrode means conductively connected to a distal end of the lead for providing a low polarization, low capacitance, low resistance and low impedance electrical interface with body fluid and/or excitable tissue in contact with or in the immediate vicinity of the electrode means when the lead assembly is implanted in a desired location in the body, said electrode means comprising
    a multiplicity of uninsulated, individual, nonmetallic, substantially isotropic electrical current conducting fibers, and maintaining means for holding the multiplicity of fibers in a flexible configuration adapted to form the said electrical interface along an entire substantial length of electrically uninsulated surface of the flexible configuration created by said multiplicity of fibers, said flexible configuration having a shape and size selected according to the site of the said electrical interface when the lead assembly is implanted in the desired location in the body, said multiplicity of fibers together providing an effective surface area for the said electrical interface which is considerably larger than the apparent actual surface area of the flexible configuration determined from the linear dimensions of the flexible configuration.

14. The invention of claim 13, wherein
said maintaining means includes the fibers themselves.

15. The invention of claim 14, wherein
said maintaining means comprises an interweaving of the fibers.

16. The invention of claim 15, wherein
the fibers are interwoven to form a substantially two-dimensional shape of the flexible configuration.

17. The invention of claim 16, wherein the biomedical use of the lead assembly is for defibrillation of the heart, and
the fibers are interwoven to form a substantially flat patch electrode means, in which the large effective surface area of the said electrical interface is adapted to enhance the efficiency of electrical energy transfer across the electron-ion boundary of the fibers and the body fluid and/or excitable tissue at the said electrical interface.

18. The invention of claim 15, wherein
the fibers are interwoven to form a three-dimensional shape of the flexible configuration.

19. The invention of claim 18, wherein the biomedical use of the lead assembly is for defibrillation of the heart, and
the fibers are interwoven to form an at least partially tubular transvenous electrode means, in which the large effective surface area of the said electrical interface is adapted to enhance the efficiency of electrical energy transfer across the electron-ion boundary of the fibers and the body fluid and/or excitable tissue at the said electrical interface, and the smaller apparent actual surface area of the flexible configuration is adapted to facilitate the introduction of the electrode means transvenously into the body.

20. The invention of claim 19, wherein
the interwoven fibers of the tubular transvenous electrode means cross over and under each other to enable axial expansion and contraction of the flexible configuration and thereby enhance the strength of the tubular transvenous electrode means against fatigue while implanted for defibrillation over time.

21. The invention of claim 13, wherein
the fibers are composed of a substantially isotropic electrically conductive carbon derivative, and have thicknesses less than about 40 microns.

* * * * *